US008603028B2

(12) United States Patent
Mudd et al.

(10) Patent No.: US 8,603,028 B2
(45) Date of Patent: Dec. 10, 2013

(54) INJECTION DEVICE HAVING AN ANGLED TIP PORTION

(75) Inventors: Christopher S. Mudd, Ventura, CA (US); Mitchell H. Babkes, Santa Clarita, CA (US); Zachary P. Dominguez, Santa Barbara, CA (US); Michael J. Prichard, Carlisle, MA (US); Martha E. Llewellyn, Maynard, MA (US); Shaohui Qiu, Belmont, MA (US); Lee F. Powers, Somerville, MA (US); Brett R. Johnson, Roseville, MN (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/422,919

(22) Filed: Mar. 16, 2012

(65) Prior Publication Data

US 2013/0131589 A1 May 23, 2013

Related U.S. Application Data

(60) Provisional application No. 61/561,748, filed on Nov. 18, 2011, provisional application No. 61/561,752, filed on Nov. 18, 2011.

(51) Int. Cl.
*A61M 37/00* (2006.01)

(52) U.S. Cl.
USPC .......... 604/82

(58) Field of Classification Search
USPC .......... 604/82, 154, 155
See application file for complete search history.

(56) References Cited

U.S. PATENT DOCUMENTS

| | | | |
|---|---|---|---|
| 2,737,946 | A | 3/1956 | Hein, Jr. |
| 2,853,070 | A | 9/1958 | Maurice |
| D202,754 | S | 11/1965 | Naftolin |
| D214,112 | S | 5/1969 | Langdon |
| D224,066 | S | 6/1972 | McDonald |
| 3,720,211 | A | 3/1973 | Kyrias |
| 3,807,048 | A | 4/1974 | Malmin |
| 4,240,423 | A | 12/1980 | Akhavi |
| 4,240,426 | A | 12/1980 | Akhavi |
| 4,273,122 | A | 6/1981 | Whitney et al. |
| 4,326,517 | A | 4/1982 | Whitney et al. |
| 4,529,401 | A | 7/1985 | Leslie et al. |
| 4,699,612 | A | 10/1987 | Hamacher |
| D303,010 | S | 8/1989 | Jabbusch |
| 4,869,717 | A | 9/1989 | Adair |
| 5,024,656 | A | 6/1991 | Gasaway et al. |
| 5,046,506 | A | 9/1991 | Singer |
| 5,100,390 | A | 3/1992 | Lubeck et al. |
| 5,127,436 | A | 7/1992 | Campion et al. |
| 5,141,496 | A | 8/1992 | Dalto et al. |

(Continued)

FOREIGN PATENT DOCUMENTS

| | | |
|---|---|---|
| EP | 0362484 | 4/1990 |
| EP | 1051988 | 11/2000 |

(Continued)

*Primary Examiner* — Aarti B Berdichevsky

(74) *Attorney, Agent, or Firm* — Linda Fox; Stephen Donovan; Debra Condino

(57) ABSTRACT

In one embodiment, the handheld injection device includes a first housing having a first axis and a second housing having a second axis. In one embodiment, the second housing is configured to support a needle. In one embodiment, the first axis and a second axis form an adjustable angle between about 180 degrees and about 90 degrees.

6 Claims, 7 Drawing Sheets

(56) References Cited

U.S. PATENT DOCUMENTS 5,295,980 A 3/1994 Ersek
5,305,788 A 4/1994 Mayeux
5,322,511 A 6/1994 Armbruster et al.
5,344,407 A 9/1994 Ryan
5,383,851 A 1/1995 MacKinnon, Jr. et al.
5,405,330 A 4/1995 Zunitch et al.
D378,939 S 4/1997 Smith et al.
5,690,618 A 11/1997 Smith et al.
5,817,033 A 10/1998 DeSantis et al.
5,891,106 A * 4/1999 Butuzov et al. ............... 604/209
D424,194 S 5/2000 Holdaway et al.
D441,077 S 4/2001 Garito et al.
6,231,552 B1 5/2001 Jentzen
6,277,102 B1 * 8/2001 Carilli ........................... 604/240
6,432,046 B1 8/2002 Yarush et al.
6,613,010 B2 9/2003 Castellano
6,616,448 B2 9/2003 Friedman
D483,116 S 12/2003 Castellano
6,689,095 B1 2/2004 Garitano et al.
6,783,514 B2 8/2004 Tovey et al.
6,824,526 B2 11/2004 Castellano
7,018,356 B2 3/2006 Wise et al.
7,419,472 B2 9/2008 Hibner et al.
7,494,473 B2 2/2009 Eggers et al.
D615,192 S 5/2010 Mudd et al.
7,878,981 B2 2/2011 Strother et al.
D637,287 S 5/2011 Mudd et al.
8,029,460 B2 10/2011 Rush et al.
8,066,629 B2 11/2011 Dlugos
2002/0010433 A1 1/2002 Johnson et al.
2002/0151843 A1 10/2002 Correa et al.
2003/0144632 A1 7/2003 Hommann et al.
2003/0199883 A1 10/2003 Laks
2004/0092927 A1 5/2004 Podhajsky et al.
2004/0147883 A1 7/2004 Tsai
2005/0085767 A1 4/2005 Menassa
2005/0131353 A1 6/2005 Mossanen-Shams et al.
2005/0137496 A1 6/2005 Walsh et al.
2005/0261633 A1 11/2005 Khalaj
2006/0079765 A1 4/2006 Neer
2006/0089594 A1 4/2006 Landau
2007/0083155 A1 4/2007 Muller
2007/0100363 A1 5/2007 Dollar et al.
2007/0212385 A1 9/2007 David
2007/0250010 A1 10/2007 Hohlfelder et al.
2008/0033347 A1 2/2008 D'Arrigo et al.
2008/0097325 A1 4/2008 Tanaka et al.
2008/0108952 A1 5/2008 Horvath et al.
2008/0188816 A1 8/2008 Shimazaki et al.
2008/0200758 A1 8/2008 Orbay et al.
2009/0088703 A1 4/2009 Azar
2009/0124996 A1 5/2009 Heneveld et al.
2009/0143746 A1 6/2009 Mudd et al.
2009/0240200 A1 9/2009 Heneveld et al.
2009/0299328 A1 * 12/2009 Mudd et al. .................. 604/506
2010/0069848 A1 3/2010 Alferness et al.
2010/0152675 A1 6/2010 McClintock
2010/0280488 A1 11/2010 Pruitt et al.
2011/0021905 A1 1/2011 Patrick et al.
2011/0137286 A1 * 6/2011 Mudd et al. .................. 604/506
2011/0160674 A1 6/2011 Holmes et al.
2011/0288481 A1 * 11/2011 Mudd et al. .................. 604/131

FOREIGN PATENT DOCUMENTS

EP 1486218 12/2004
EP 1859827 11/2007
EP 1923086 5/2008
EP 2335755 6/2011
FR 2622457 5/1989
WO WO 99/48601 9/1999
WO WO 2008/019265 2/2008
WO WO 2008/079824 7/2008
WO WO 2009/098666 8/2009
WO WO 2009/0158145 12/2009

* cited by examiner 204
206
201
202
208
203
210
200

304
300
302
306
308

300
302
θ
306
308
310

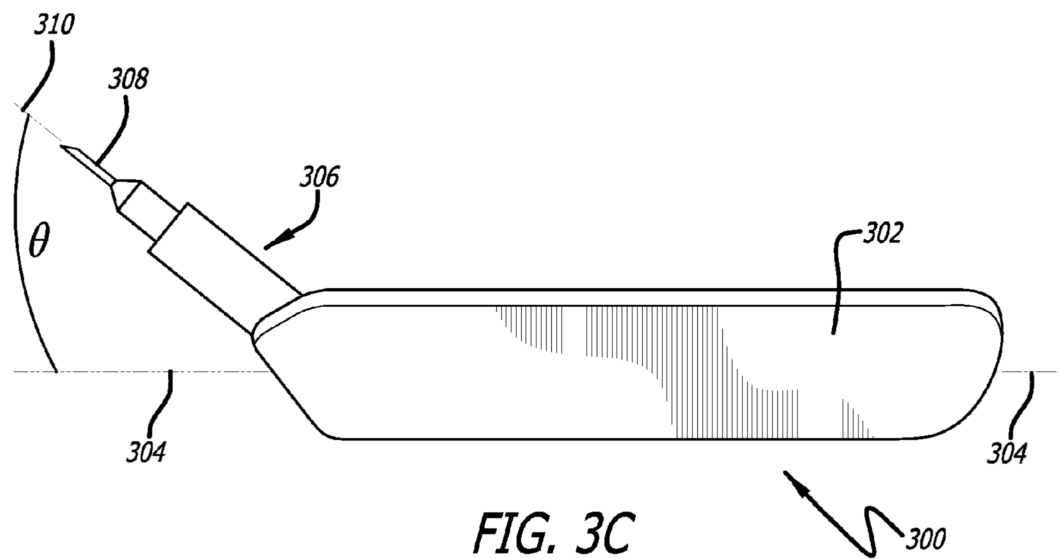
FIG. 3C
FIG. 3D
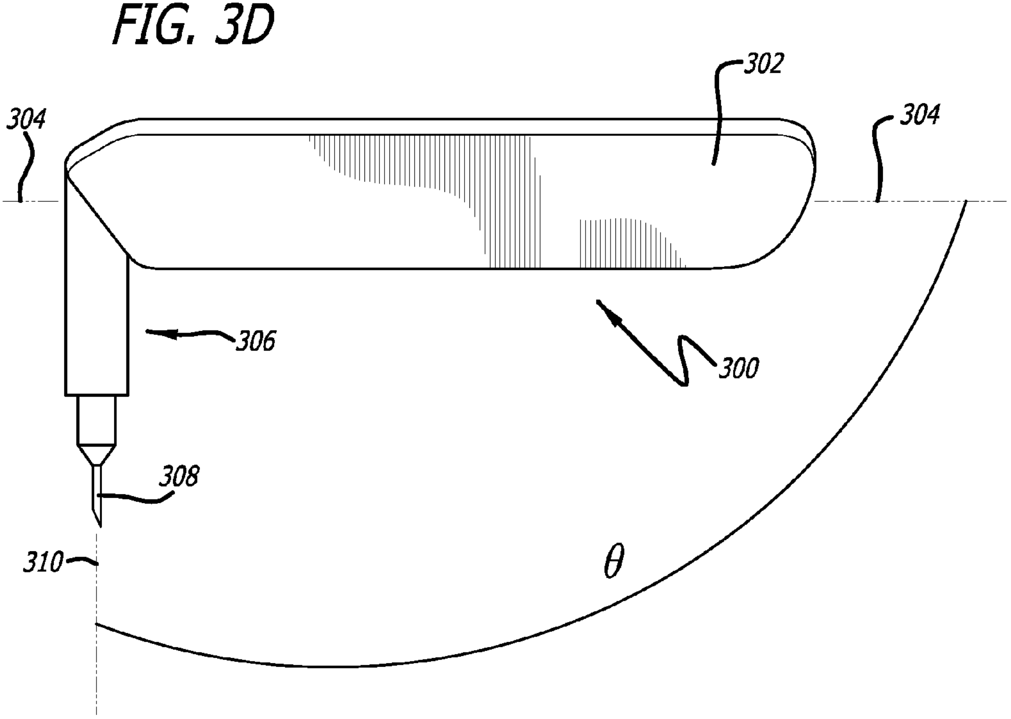

4B
4C
404
408
406
412
414
416
418
420
410
406
4C
4B
402
400

408
412
418
420

410
412

414
404
406
404
408

410
416

INJECTION DEVICE HAVING AN ANGLED TIP PORTION

CROSS REFERENCE TO RELATED APPLICATIONS

This application claims the benefit of U.S. Provisional Patent Application No. 61/561,748, filed Nov. 18, 2011, and U.S. Provisional Patent Application No. 61/561,752, filed Nov. 18, 2011, the entire disclosures of which are incorporated herein by this reference.

BACKGROUND

A number of medical and cosmetic applications and treatments involve controlled injection of substances into the body.

A medical syringe is a simple piston pump consisting of a plunger that fits tightly in a cylindrical barrel. The plunger can be pulled and pushed along inside the barrel, allowing the syringe to take in and expel a fluid through an orifice at the distal open end of the barrel. The distal end of the syringe is typically fitted with a hypodermic needle to introduce the barrel's fluid into a patient. Surprisingly, other than the materials used to make a syringe, the typical disposable syringes are much the same as the very earliest syringe designs.

Unfortunately, classic syringe/needle systems are far from optimal for the administration of today's injectable aesthetic compositions. Hydrogel-based dermal fillers can be quite difficult to inject using the conventional syringe/needle system or conventional injection techniques. Many dermal fillers are by their nature highly viscous, thus requiring relatively high extrusion forces, especially when injected through preferred fine gauge needles. Moreover, these materials are typically injected into the face to correct wrinkles, including fine wrinkles as well as other minor defects in skin, and therefore, must be sometimes injected in trace amounts, and always with very high precision. Interestingly, these dermal fillers are commonly introduced into skin using quite standard needle and syringe combinations.

Using a traditional syringe and needle combination, physicians can be required to apply the needle at a shallow angle relative to the skin of a patient. It can be difficult to precisely control the needle to a predetermined location during an injection. Accordingly, a need exists for further development of injection devices.

SUMMARY

In one embodiment, the handheld injection device includes: (a) a first housing having a first axis; (b) a processor; (c) an input device operatively coupled to the processor; (d) a first chamber configured to contain a first injectable fluid; (e) a second chamber configured to contain a second injectable fluid; (f) a drive unit operatively coupled to the processor; (g) a second housing configured to support a needle having a second axis, the second housing being positioned such that the first axis and the second axis form an angle greater than 0; and (h) a memory device storing instructions. In operation, the injection device can select a dilution ratio of the first injectable liquid to the second injectable liquid. In one embodiment, the injection device can, based on the selected dilution ratio, produce an injectable mixed fluid by diluting the first injectable liquid with the second injectable liquid. Thereafter, using the drive unit, the injection device extrudes the injectable mixed fluid.

In one embodiment, the angle is adjustable. In another embodiment, the angle is fixed.

In one embodiment, the angle is adjustable based on the second housing being configured to be able to rotate between a plurality of fixed predetermined positions.

In one embodiment, the angle is adjustable based on the second housing being configured to be able to continuously rotate between a range of positions.

In one embodiment, the injection device includes an O-ring. In one embodiment, after a specific angular orientation is set, the O-ring is configured to set and provide a holding force.

In one embodiment, the angle is adjustable in at least one of: (a) a vertical direction; (b) a horizontal direction; and a diagonal direction.

Additional features and advantages are described herein, and will be apparent from, the following Detailed Description and Figures.

BRIEF DESCRIPTION OF THE DRAWINGS

FIGS. 3A, 3B, 3C AND 3D illustrate perspective views of one embodiment of the injection device disclosed herein, illustrating an example range of angles formed between the axis of the housing and the axis of the cartridge portion or needle.

DETAILED DESCRIPTION

Figure 1A:
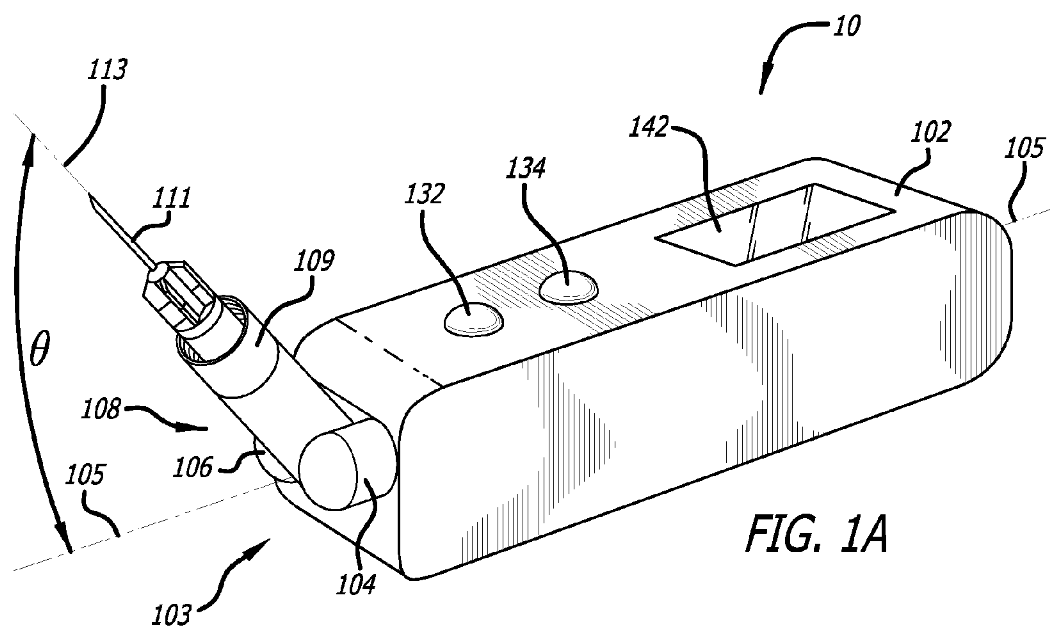
FIG. 1A illustrates a perspective view of one embodiment of the injection device disclosed herein, illustrating the housing of the injection device.

Described herein generally are injection devices having an angled tip portion. In one embodiment, the injection device includes: (a) cartridges configured to contain injectable fluids; (b) a control system; and (c) an injection drive mechanism or a drive unit configured to cause: (i) the injectable fluids to be extruded; and (d) an adjustable tip portion which may be adjusted using the control system. In one embodiment, the injection device includes a fixed tip portion.

In the general operation of one embodiment, before an injection occurs, the injection device can enable a user to select a desired tip angle. As mentioned above, a number of medical and cosmetic procedures involve the controlled injection of liquids, gels, and other fluids. For instance, procedures involving the injection of botulinum toxin or the injection of dermal fillers may require highly controlled injections. Using the injection devices with angled tips disclosed herein, users are provided with more control during an injection procedure.

FIGS. 1, 2, 3A, 3B, 5A and 5B depict different injection devices having tip portions (e.g., the adjustable tip portion and the fixed tip portion). The tip portions described herein can be employed by any suitable injection device, such as the injection devices described in U.S. Patent Application No. 61/561,748 and U.S. Patent Application No. 61/561,752. Those patent applications are in the name of Allergan, Inc. and are hereby incorporated into this specification by reference. The incorporation of the above-mentioned patents does not and should not be construed as an admission of the content of the specification having entered the common general knowledge of those skilled in the art.

Referring now to FIGS. 1A through 1D, in one embodiment, injection device 10 includes: (a) housing or body 102; (b) adjustable cartridge 103; (c) drive unit 110; (d) control system 112 having: (i) processor 114; (ii) memory device 116; and (iii) input/output devices 118.

Figure 1B:
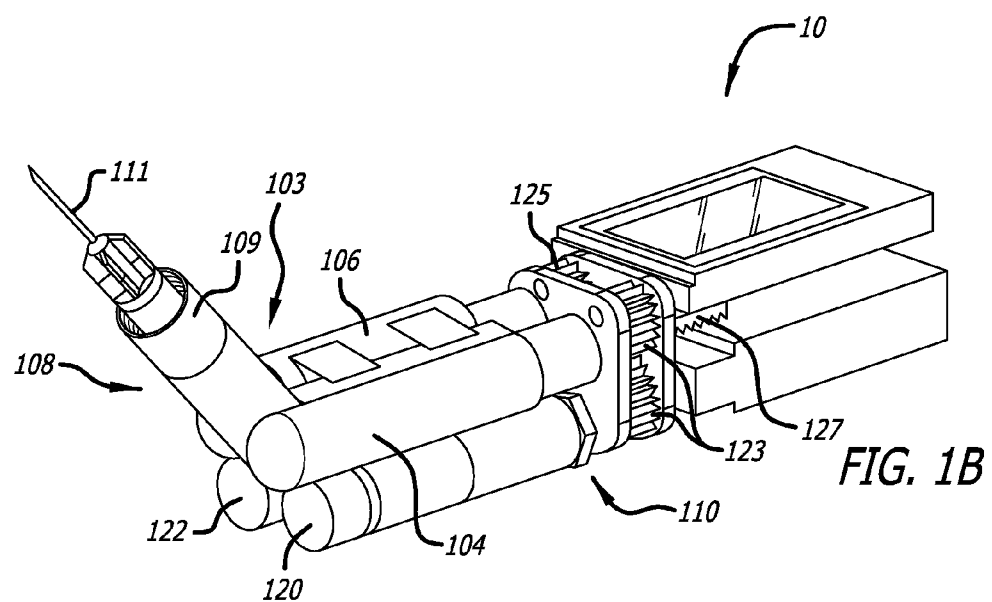
FIG. 1B illustrates a perspective view of one embodiment of the injection device discloses herein, illustrating the drive unit.
Figure 1C:
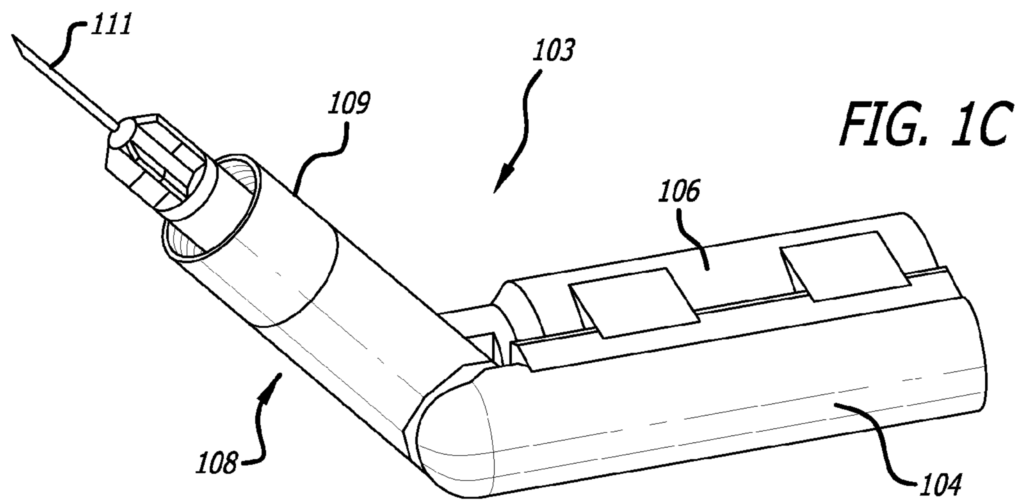
FIG. 1C illustrates a perspective view of one embodiment of the adjustable cartridge, illustrating the cartridge portion being rotatable around the cartridges.

As illustrated in FIGS. 1B and 1C, in one embodiment, adjustable cartridge 103 includes: (a) first cartridge 104 defining a first chamber which is configured to contain a first injectable fluid; (b) second cartridge 106 defining a second chamber which is configured to contain a second injectable fluid; and (c) cartridge portion 107 configured to: (i) rotate around the front portions of first cartridge 104 and second cartridge 106; and (ii) support needle 111. In one embodiment, cartridge portion 107 includes housing 109 (e.g., a second housing). In another embodiment, housing 109 is configured to support needle 111.

As illustrated in FIG. 1A, in one embodiment, housing 102 of injection device 10 has first axis 105 and needle 111 has second axis 113. In one embodiment, cartridge portion 107 has a third axis which runs parallel to second axis 113. It should be appreciated that in FIG. 1A, an angle greater than zero is formed between: (a) first axis 105 and second axis 113; and (b) first axis 105 and the axis of cartridge portion 107. In FIG. 1A, as shown at 8, the angle formed between first axis 105 and second axis 113 is about 45 degrees.

In one embodiment, adjustable cartridge 103 includes needle 111. In an alternate embodiment, adjustable cartridge 103 is separate from and configured to attach to needle 111. In one embodiment, using a luer tip, adjustable cartridge 103 is coupled to needle 111. It should be appreciated that, in different examples, injection device 10 is configured to include or attach to any suitable cartridge. The needle itself may have any suitable gauge, for example, a gauge between about 10 and about 33. In one embodiment, the needle is a 30G×¾" needle.

As illustrated in FIG. 1B, in this embodiment, drive unit 110 includes first gear motor 120 and second gear motor 122. First gear motor 120 is operatively connected to first gear 123, and second gear motor 122 is operatively connected to second gear 125. In this example, drive unit 110 also includes: (a) first rack 127 which is operatively engaged with first gear 123 and a first plunger; and (b) a second rack which is operatively engaged with second gear 125 and a second plunger. Drive unit 110 illustrated in FIG. 1B may provide an effectively infinite number of dilution ratios and injection speeds by independently setting the speed of one gear motor relative to another gear motor.

In operation, in this example, drive unit 110 drives the linear motion of the plungers which causes fluids to be extruded. More specifically, first gear motor 120 causes first gear 123 to turn, thereby driving the linear motion of first rack 127. First rack 127 engages the first plunger, thereby causing the first injectable fluid to flow from the first chamber to cartridge portion 108 to be extruded through the needle. Second gear motor 122 causes second gear 125 to turn, thereby driving the linear motion of the second rack. The second rack engages the second plunger, thereby causing the second injectable fluid to flow from the second chamber to cartridge portion 108 to be extruded through the needle.

In one embodiment, the rotational output of the motors drives the linear motion of the racks through worm gears. In another example, the rotational output of the motors drives the linear motion of the racks through concentric gearing of an internally threaded gear to a threaded rack.

In different embodiments, the drive unit may include a single gear motor and a transmission, a pressure driven system, a hydraulically driven system, or a nitinol driven system.

It should be appreciated that any of the motors discussed herein may be any suitable electric motor capable of supplying the necessary force. In one embodiment, the motors are operatively connected to the plungers via certain of the drive units discussed herein. In some examples, the drive units function to transfer the rotational motion of the motors into the linear motion of the plunger.

In one embodiment, the injection device includes a control system. In one embodiment, the control system may include at least one processor, at least one memory device operatively connected to the at least one processor, at least one input device operatively connected to the at least one processor, and at least one output device operatively connected to the at least one processor.

The at least one processor may be any suitable processor unit of a kind normally used in such devices. In one embodiment, the control system includes one or more digital processors, such as a digital microprocessor or a micro-controller based platform. In one embodiment, the control system includes one or more analog control units such as a suitable integrated circuit or one or more application-specific integrated circuits (ASIC's). In one embodiment, the control system is in communication with, or operable to access or exchange signals with the at least one memory device. In this example, the memory device stores program code or instructions, executable by the processor(s), to control the injection device. In one embodiment, such memory device includes: (a) RAM (MRAM); (b) ferroelectric RAM (FeRAM); (c) read only memory (ROM); (d) flash memory; (e) EEPROM (electrically erasable programmable read only memory); or a suitable combination of such memory devices. It should be appreciated that any other suitable magnetic, optical, or semiconductor memory may operate in conjunction with, or as part of, the injection device.

In one embodiment, the output devices include at least one display device. In one embodiment, the display device includes an LCD screen which is located on a front of the injection device, and allows a user to interact with the system. In one embodiment, the display device includes an interface. Using the interface, the user may control the operation of the device.

The injection device may be configured to cause the display device to display at least one of, for each fluid contained: (i) the volume that has been injected; (ii) the volume remaining; (iii) the starting volume; and (iv) the speed or injection rate. The display device may also display at least one of: (a) the total volume of fluid that has been extruded or injected; (b) the speed or rate of injection of the mixed fluid; (c) the dilution ratio of the fluid being injected; and (d) the angle formed between the first axis and the second axis. In addition, other information may be displayed to facilitate different functions. For instance, the display device may also display configuration screens, summary information, error indicators in the case of a malfunction, and/or battery power information.

In one embodiment, the input devices include an inject button. The inject button may be located on injection device 10 in a position which is conveniently accessible by a user's fingers or thumb during injection. The inject button may start and stop the injection process. In one embodiment, the user may press and hold the inject button to begin the injection, and may release the inject button to stop the injection. In other examples, the injection process may work in other ways. For instance, the user may press the inject button once to begin the injection and a second time to stop the injection.

In one embodiment, control system 112 includes at least one input device (e.g., a keypad, a button, a dial or a switch) which enables a user to control the overall speed or rate or volume of the extrusion. In one embodiment, control system 112 includes at least input device (e.g., a button, dial or switch) which enables a user to control the overall speed or rate or volume of the injection by enabling the user to independently control the speed or rate or volume of the injection of each injectable fluid.

In one embodiment, the injection device is configured to extrude fluid at a plurality of predetermined selectable speeds. As described in more detail below, in one embodiment, the injection device is configured to extrude fluid at the following four different selectable speeds: very low, low, medium and high. In one embodiment, the injection device is configured to extrude fluid at a dynamic speed which enables extrusion of each of the four different speeds based on the amount of pressure exerted on the inject button. Lighter pressure on the inject button will correspond to a lower injection speed and a higher pressure will correspond to a higher injection speed. The approximate corresponding flow rates are shown in Table 1.

These flow rates were determined based on evaluation physician's typical extrusion rates.

TABLE 1

| Injection Rates | |
|---|---|
| Speed Setting | Injection Rate (mL/minute)* |
| Very Low | 0.30 |
| Low | 0.60 |
| Medium | 0.90 |
| High | 1.20 |
| Dynamic | 0.30-1.20 |

*APPROXIMATE INJECTION RATE

In one embodiment, the input devices include at least one encoder. Using at least one encoder, the injection device determines the position of the plungers. In one embodiment, using the at least one encoder, the injection device determines and displays volume information of each contained fluid and/or the total volume extruded/injected.

In one embodiment, the encoder is rotational encoder connected to a motor. In this example, the rotational encoder is configured to sense the rotation of the motor. For example, the motor may rotate a portion of the rotational encoder.

In different examples, other portions of the injection device may be encoded. For example, in one embodiment, the injection device includes a separate linear encoder for each of the plungers.

Figure 1D:
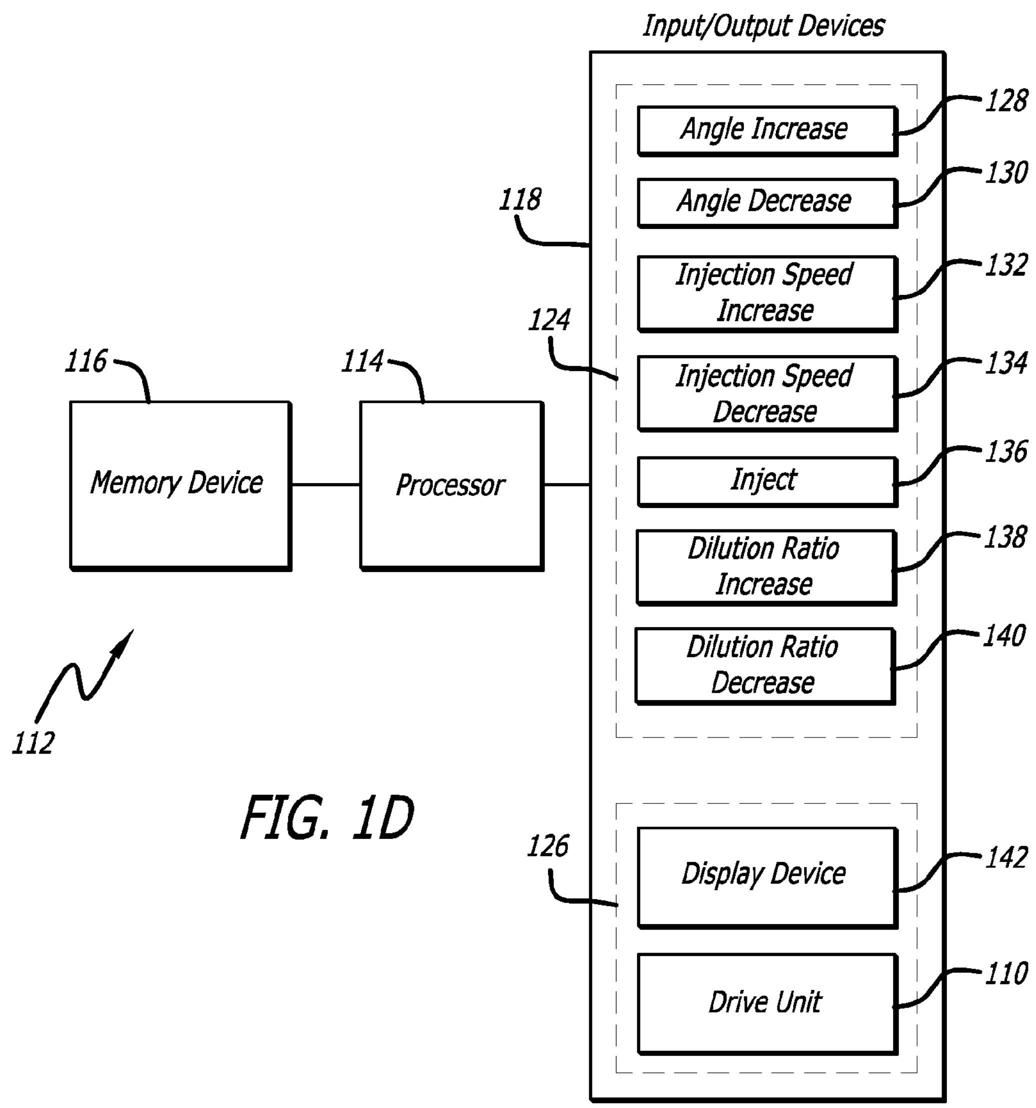
FIG. 1D illustrates a schematic diagram of one embodiment of the control system, illustrating the processor, the memory device, the input devices and the output devices.

Referring to FIG. 1D, control system 112 includes: (a) at least one processor 114; (b) at least one memory device 116 operatively connected to processor 114; (c) input devices 124 operatively coupled to processor 114; and (d) output devices 126 operatively coupled to processor 114. In one embodiment, as illustrated in FIG. 1D, input devices 124 include: (a) angle increase button 128; (b) angle decrease button 130 (c) injection speed increase button 132; (d) injection speed decrease button 134; (e) inject button 136; (a) dilution ratio increase button 138; (b) dilution ratio decrease button 140. Output devices 126 include: (a) display device 142; and (b) drive unit 110. Control system 115 may be a portion of a control system for the injection device (not shown).

In one embodiment, the user is enabled to control the angle formed between the axis of the housing of the injection device and the axis of the cartridge portion or needle by selecting angle increase button 128 and angle decrease button 130. In this embodiment, the selection of angle increase button 128 causes injection device 10 to drive cartridge portion 108 such that the angle between the axis of cartridge portion 108 and the axis of housing 102 increases. The selection of angle decrease button 130 causes injection device 10 to drive cartridge portion 108 such that the angle between the axis of cartridge portion 108 and the axis of housing 102 decreases. In one embodiment, using the angle increase button 128 and angle decrease button 130, the user is enabled to control the movement of cartridge portion 108 such that the angle formed between the axis of the housing of the injection device and the axis of the cartridge portion 108 is adjustable between about 180 degrees and about 90 degrees. When performing an injection, the use of an angled tip can provide a user better control of the injection device.

In one embodiment, the user is enabled to control the specific injection rate speed by selecting injection speed increase button 132 and injection speed decrease button 134.

In different examples, injection device 10 may be ergonomically designed to facilitate injection for a wide variety of hand shapes, sizes and gripping positions. Advantageously, the injector device may be easy to manipulate and grip. In alternative embodiments, heavier components of the device are housed in the different positions of the injection device.

Figure 2:
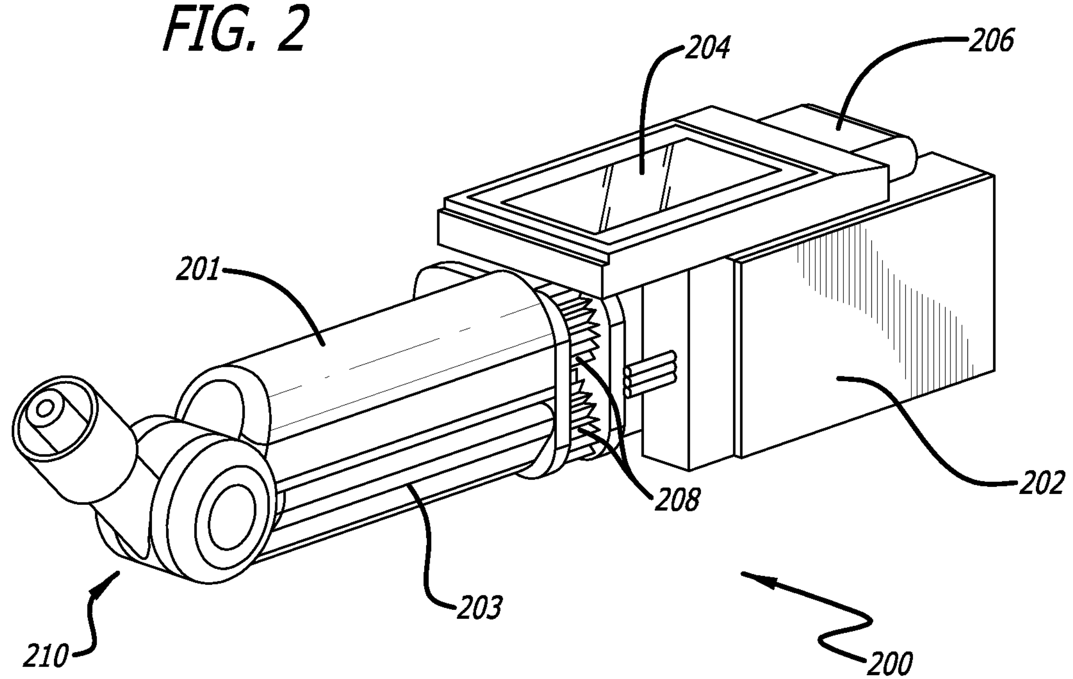
FIG. 2 illustrates a perspective view one embodiment of an injection device disclosed herein, illustrating a potentially unobstructed viewing of the cartridges by positioning certain components of the injection device in the rear section of the injection device.

FIG. 2 illustrates a different component configuration which may provide a more balanced device (e.g., weight balance, ergonomically balanced, etc.) and facilitate injection for a wide variety of hand shapes, sizes and gripping positions. In this embodiment, the components of injection device 200 are configured to allow for potentially unobstructed viewing of first cartridge 201 and second cartridge 203 by positioning most of the components of injection device 200 in the rear section of injection device 200. The following components of injection device 200 illustrated in FIG. 2 are positioned in the rear section: (a) battery 202; (b) first motor (not shown); (b) second motor (not shown); (c) first rack (not shown); (d) second rack (not shown); (e) display device 204; and (i) circuit board 206. As illustrated in FIG. 2, injection device 200 also includes first gear 208 and adjustable tip portion 210. In this example, injection device 200 is rear heavy, and allows for a narrow cross section at the position where a user's fingers would grip the injection device 200.

Figures 3A, 3B:
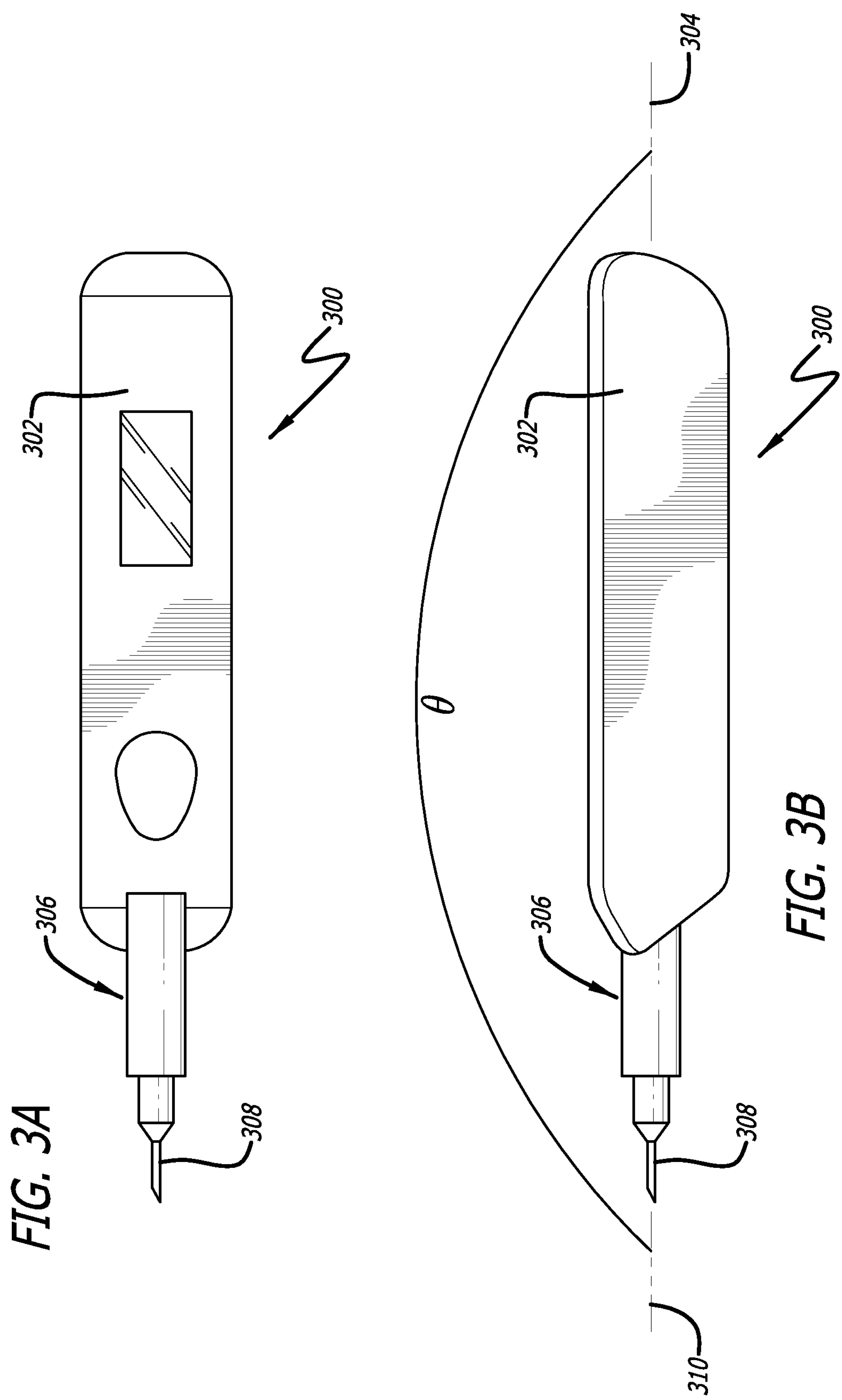

FIGS. 3A to 3D illustrate perspective views of one embodiment of the injection device disclosed herein, illustrating an example range of angles formed between the axis of the housing and the axis of the cartridge portion or needle. As illustrated in FIGS. 3A to 3D, injection device 300 includes: (a) housing 302 having first axis 304; and (b) adjustable tip portion 306 and needle 308 having second axis 310. In FIG. 3B, adjustable tip portion 302 forms a 180 degree angle with housing 306. That is, as shown at θ, the angle formed between first axis 304 and second axis 310 is 180 degrees. FIG. 3C illustrates adjustable tip portion 306 having a position different from the position shown in FIG. 3B. In FIG. 3C, adjustable tip portion 302 forms a 45 degree angle with housing 306. That is, as shown at θ, the angle formed between first axis 304 and second axis 310 is 45 degrees. FIG. 3D illustrates adjustable tip portion 306 having a position different from the position shown in FIGS. 3B and 3C. In FIG. 3D, adjustable tip portion 302 forms a 90 degree angle with housing 306. That is, as shown at θ, the angle formed between first axis 304 and second axis 310 is 90 degrees. In this example, the adjustable tip portion is configured rotate between a plurality of positions It should be appreciated that the angles formed by any of the above-mentioned axes can be measured from left to right or right to left. For example, as illustrated in FIG. 3C, the angle formed between first axis 304 and second axis 310 can be expressed as either 45 degrees or 135 degrees based on whether the angle is measured left to right, or right to left.

Figure 4A:
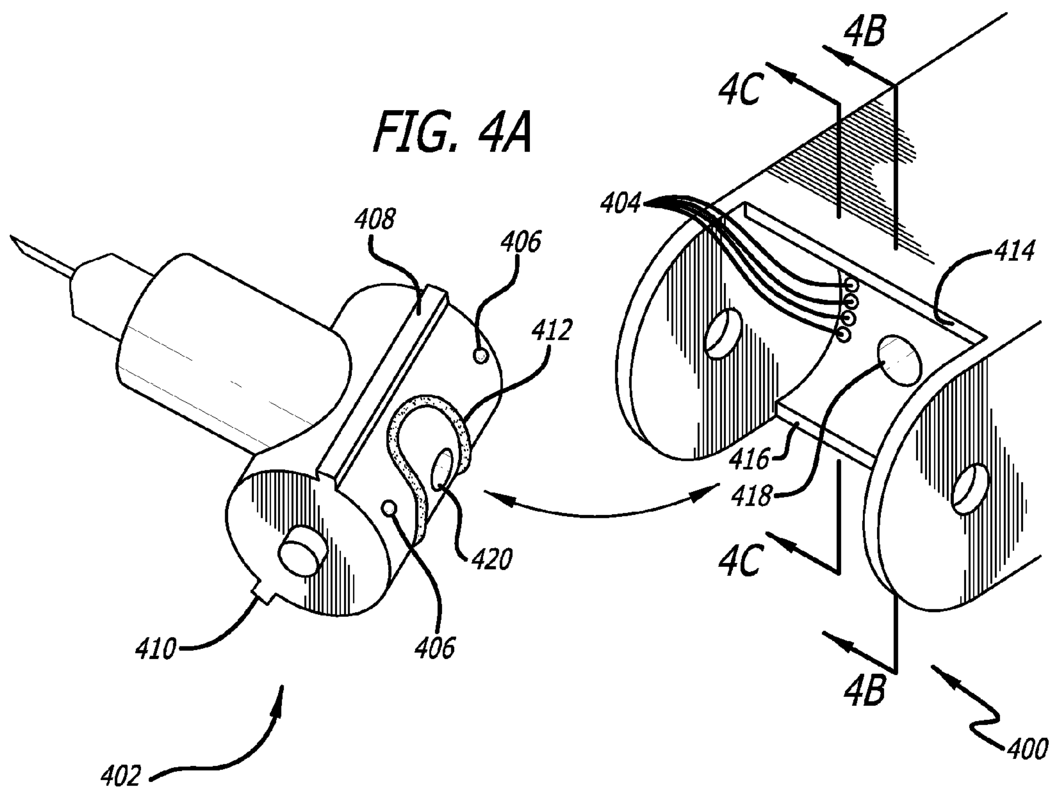
FIGS. 4A, 4B and 4C illustrate views of one embodiment of the injection device disclosed herein, illustrating the adjustable tip portion being configured to adjust at a plurality of predetermined fixed positions.
Figure 4B:
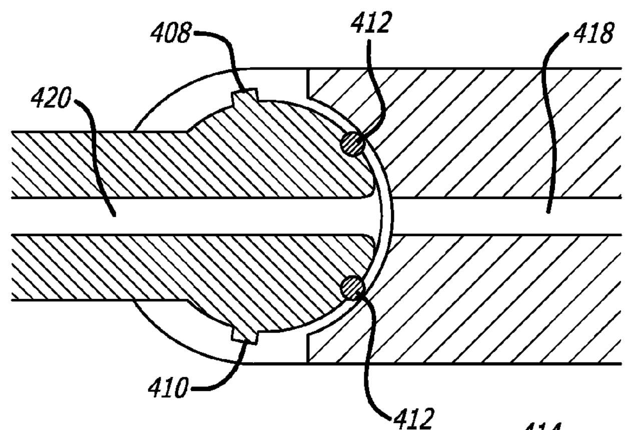
Figure 4C:
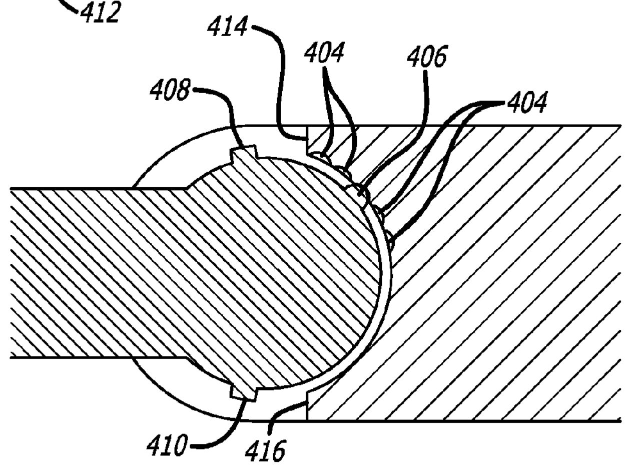

In one example, the tip portion of the injection device is configured to rotate at a plurality of predetermined fixed positions. For example, referring to FIGS. 4A to 4C, injection device 400 includes adjustable tip portion 402 which is configured to adjust at a plurality of predetermined fixed positions. Specifically, in this embodiment, injection device 400 includes: (a) spaced out depressions 404; (b) ball bearings 406 which are configured to engage with spaced out depression 404; (c) first projection 408; (d) second projection 410; (e) O-ring 412; (f) first edge portion 414; and (g) second edge portion 416. Injection device 400 defines first channel 418 and second channel 420. In this embodiment, a seal is formed using O-ring 412 such that when fluid is extruded, the fluid is caused to flow from first channel 418 through second channel 420 and out of the needle. That is, the fluid is prevented from leaking from injection device 400 at position which the housing of the injection device meets adjustable tip portion 402. By contacting first projection 408, first edge portion 414 is configured to stop adjustable tip portion 402 from moving in an up direction. Similarly, by contacting second projection 416, second edge portion 416 is configured to stop adjustable tip portion 402 from moving in a down direction.

In one embodiment, the injection device includes at least one O-ring which sets to provide a holding force once a specific angular orientation is set. In one embodiment, the injection device a feature such a detent which provides feedback and an additional holding force when a specific angle is achieved.

Figure 5A:
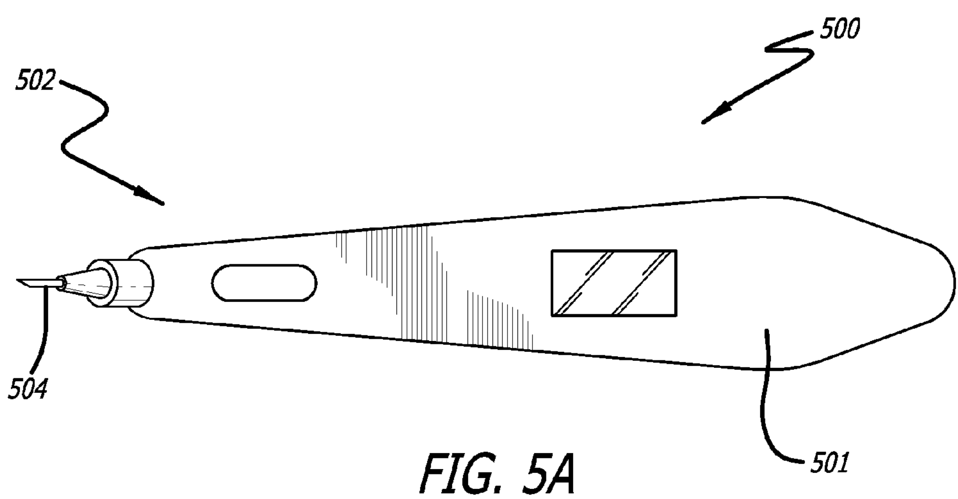
FIGS. 5A and 5B illustrate a perspective view of one embodiment of the injection device disclosed herein, illustrating the injection device having a fixed angle.
Figure 5B:
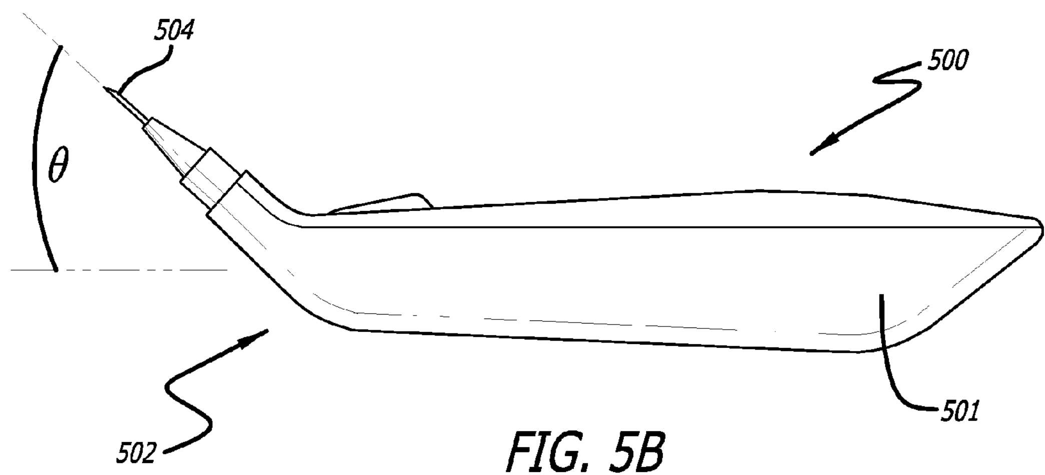

In one embodiment, the injection device includes a fixed tip portion. For example, as illustrated in FIGS. 5A and 5B, injection device 500 includes a fixed tip portion 502. In this embodiment, injection device 500 includes housing 501 and needle 504. It should be appreciated that in FIGS. 5A and 5B, an angle greater than zero is formed between the axis of the needle and the housing of the injection device. In this embodiment, needle 504 has an axis which forms about a fixed 45 degree angle with respect to the angle of housing 501. It should be appreciated that in different embodiments, the fixed angle formed between the tip portion and the housing of the injection device can be any suitable angle greater than zero degrees. For example, in different embodiments, the formed fixed angle can range from 5 degrees to 90 degrees.

The adjustable tip portion of the injection device has been described as moving between up and down positions. In one embodiment, the adjustable tip portion of the injection is configured to swivel from the body of the injection device. That is, the adjustable tip portion can be adjusted in a plurality of directions such as right to left, left to right, up to down, down to up, and can be adjusted in diagonal direction.

Housing 102 may have a grippable housing, which may be made of any suitable material, e.g., metals, thermoplastics, thermoplastic elastomers (TPEs), silicones, glass, etc., or any combination of materials. Housing 102 may be shaped to comfortably accommodate a user's hand. A portion of housing 102 designed to be gripped may be textured to provide a secure grip, or may be covered in a layer of material designed to provide a secure grip.

In one embodiment, the cartridge(s) is made of cyclic olefin copolymer (COC).

In one embodiment, after a desired amount of fluid has been injected into the patient, the user of the injection device may remove and discard any used cartridges along with the needle. In one embodiment, after a desired amount of fluid has been injected into the patient, the user of the injection device may remove and discard the adjustable cartridge.

In one embodiment, the injectable fluids (e.g., the first injectable fluid or the second injectable fluid) include at least one biocompatible material. These biocompatible materials include, but are not limited to, dermal fillers, hyaluronic acid-based dermal fillers (e.g., Juvederm™ Ultra and Juvederm™ Ultra Plus (Allergan, Irvine, Calif.)), hydrogels (i.e., super-absorbent natural or synthetic polymers), organogels, xerogels, encapsulated and/or cross-linked biomaterials, silicones, glycosaminoglycans (e.g., chondroitin sulfate, dermatin sulfate, dermatin, dermatin sulfate, heparin sulfate, hyaluronic acid, o-sulfated hyaluronic acid), polysaccharides (e.g., chitosan, starch, glycogen, cellulose), collagen, elastin, local anesthetics (e.g., Benzocaine, Chloroprocaine, Cyclomethycaine, Dimethocaine/Larocaine, Propoxycaine, Procaine/Novocaine, Proparacaine, Tetracaine/Amethocaine, Amino amides, Articaine, Bupivacaine, Carticaine, Cinchocaine/Dibucaine, Etidocaine, Levobupivacaine, Lidocaine/Lignocaine, Mepivacaine, Piperocaine, Prilocalne, Ropivacaine, Trimecaine), drugs, bioactive agents, antioxidants, enzyme inhibitors (e.g., anti-hyaluronidase), vitamins, minerals, water, saline, light curable or light activated materials, vaccines, and pH curable or pH activated materials. Other biocompatible materials not mentioned above are also considered within the scope of the present description.

In one embodiment, the second injectable fluid includes a bioactive agent which facilities delivery of the first injectable fluid injection (e.g., to reduce extrusion force and/or viscosity). Additional bioactive agents may include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, anti-fungal agents, steroids, chemotherapeutic agents, analgesics, antibiotics, protease inhibitors, statins, nucleic acids, polypeptides, growth factors and delivery vectors including recombinant micro-organisms, liposomes, and the like. Combinations of additional bioactive agents are also within the scope of the present description.

Other injectable fluids (e.g., the first injectable fluid or the second injectable fluid) may include toxins such as botulinum toxins. The botulinum toxin can be selected from the group consisting of botulinum toxin types A, B, $C_1$, D, E, F and G, a pure or purified (i.e., about 150 kD) botulinum toxin, as well as a native or recombinant botulinum toxin. The material can comprise between about 1 unit to about 20,000 units of the botulinum toxin or a therapeutically effective amount, and the composition can comprise an amount of botulinum toxin sufficient to achieve a therapeutic effect lasting between 1 month and 5 years. The botulinum toxin can be reconstituted within the device as described elsewhere herein or before the cartridge is placed in the device. The botulinum toxin can be reconstituted with sterile 0.9% sodium chloride (saline).

In one embodiment, the dilution ratio is 1 to 100 units of botulinum toxin per 0.1 mL of saline. More preferably, in one embodiment, the dilution ratio is 1 to 50 units per 0.1 mL of saline, or 1 to 10 units per 0.1 mL of saline. In one embodiment, 4 units per 0.1 mL of saline is used. The dilution ratio will be highly dependent on the type of botulinum toxin used or combination of botulinum toxins used.

In one embodiment, cartridge portion 108 includes a mixing unit which is configured to mix the injectable fluids by directing the injectable fluids into a spiral mixing path. In one embodiment, the mixing unit is configured to mix fluids by directing the injectable fluids into a helical path. In one embodiment, the mixing unit includes corrugated sections which are configured to mix the injectable fluids. It should also be appreciated that in different examples, the injection device may include any suitable mixing unit.

In one embodiment, the injector device determines the ratio of the first fluid and the second fluid based on the selected injection speeds of the first fluid and the second fluid. That is, in this example, the injection device enables a user to select a first injection rate for the first fluid and a second injection rate for the second fluid. After the injection rates have been selected or set, in response to the user selecting the inject button, the injection device causes each of the injectable fluids to extrude the injection device based on their selected injection rates.

In one embodiment, drive unit 110 includes a single gear motor and a transmission. In this example, the transmission's gear ratios are selected such that each gear will deliver a desired dilution ratio. In one embodiment, drive unit 110 includes a separate energy source to switch gears in the transmission. In different embodiments, the gears are switched in the transmission using an additional motor, a user operated switch, and/or a nitinol actuator. In one embodiment, using a single encoder on the single gear motor, the injection device determines the positions of the first plunger and the second plunger based on the amount of time the transmission was engaged in each gear.

In one embodiment, drive unit 110 includes a pressure driven system which includes a pressure source (e.g., a CO2 cartridge) used to drive each plunger forward. In this embodiment, the dilution ratio is determined by regulating the flow of the fluid from each cartridge. In one embodiment, the injection device enables a user to regulate each cartridge by manually control the individual flow out of the cartridges using pressure/flow regulators. In one embodiment, the injection device electronically controls the individual flow out of the cartridges using pressure/flow regulators. It should be appreciated that, where the drive unit of the injection device includes a pressure driven system, many pressure/flow regulator combinations may be used to control injection rate and dilution ratio. In this example, the injection device may determine the amount of fluid which has been injected/extruded using encoders which indicate the positions of the plungers.

In one embodiment, drive unit 110 includes a hydraulically driven system. In one embodiment, drive unit 110 includes a nitinol drive system.

In one embodiment, the input devices include at least one sensor. For example, injection device 10 may include a cartridge inserted sensor. Using the cartridge inserted sensor, the injection device may detect whether at least one cartridge is inserted in the cartridge housing. The cartridge inserted sensor may prevent the injection device from attempting to perform an injection without cartridge(s) properly loaded. In one embodiment, the injection device includes a home sensor. Using the home sensor, the injection device may detect whether the injection device is in a home state.

In one embodiment, injection device 10 includes at least one motor driver. In one embodiment, the motor driver communicates with both the processor and the motor(s). The motor driver may provide the systems necessary to control the operation of the motor(s). In one embodiment, using input from sensors and encoders, the processor directs the motor(s) through the motor driver, which in turn may control the extension of the plunger and thus the injection.

In addition, injection device 10 may include a power system. For example, injection device 10 may house at least one battery, or other power source (e.g., a rechargeable battery or a fuel cell). In one embodiment, the battery provides power to the control system. The battery may be connected to the control system in any suitable manner. For example, the battery may be permanently connected, e.g., soldered, or may be connected through a connector. In the later case, a door may be provided in the injection device, which may allow access to the battery for removal and replacement.

In addition, injection device 10 may include a battery charger. The battery charger may be capable of charging the at least one battery when connected to an external source of electricity. For example, the injector device may include a connector, which may allow the injector device to connect to a source of electrical power, such a standard 120 or 240 V AC power source. Of course, the injector device need not connect to such a power source directly. Rather the injector device may connect to a power adaptor or supply system, which may in turn connect to the primary power source. In addition, any suitable connector may be provided, e.g., in the body of the injection device, for connection to the external power source.

In the preceding specification, the present disclosure has been described with reference to specific example embodiments thereof. It will, however, be evident that various modifications and changes may be made thereunto without departing from the broader spirit and scope of the present disclosure. The description and drawings are accordingly to be regarded in an illustrative rather than restrictive sense.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A handheld injection device comprising:

a first housing having a first axis;

a processor;

an input device operatively coupled to the processor;

a first chamber configured to contain a first injectable fluid;

a second chamber configured to contain a second injectable fluid;

the first and second chambers being contained in a distal region of the first housing and disposed in a side-by-side relationship with respect to each other;

a drive unit operatively coupled to the processor;

a second housing configured to support a needle having a second axis, the second housing being rotatable with respect to the first housing and adjustably positioned such that the first axis and the second axis form an adjustable angle; and a memory device storing instructions which when executed by the processor, causes the processor, in conjunction with the input device and the drive unit, to:

(a) select a dilution ratio of the first injectable fluid to the second injectable fluid;

(b) based on the selected dilution ratio, produce an injectable mixed fluid by diluting the first injectable liquid with the second injectable liquid; and (c) extrude the injectable mixed fluid.

2. The handheld injection device of claim 1, wherein the angle is adjustable between 180 degrees and 90 degrees.

3. The handheld injection device of claim 2, wherein the angle is adjustable based on the second housing being configured to be able to rotate between a plurality of fixed predetermined positions.

4. The handheld injection device of claim 2, wherein the angle is adjustable based on the second housing being configured to be able to continuously rotate between a range of positions.

5. The handheld injection device of claim 4, which includes an O-ring, wherein, after a specific angular orientation is set, the O-ring is configured to set and provide a holding force.

6. A handheld dermal filler injection device comprising:

a first housing having a first axis;

a processor;

an input device operatively coupled to the processor;

a first chamber configured to contain a dermal filler;

a second chamber configured to contain a biocompatible fluid to be mixed with the dermal filler;

the first and second chambers being contained in a distal region of the first housing and disposed in a side-by-side relationship with respect to each other;

a drive unit operatively coupled to the processor;

a second housing configured to support a needle having a second axis, the second housing being rotatable with respect to the first housing and adjustably positioned such that the first axis and the second axis form an adjustable angle; and a memory device storing instructions which when executed by the processor, causes the processor, in conjunction with the input device and the drive unit, to:

(a) select a dilution ratio of the dermal filler to the biocompatible fluid;

(b) based on the selected dilution ratio, produce an injectable mixed fluid by diluting the dermal filler with the biocompatible fluid; and (c) extrude the injectable mixed fluid.

* * * * *

UNITED STATES PATENT AND TRADEMARK OFFICE

CERTIFICATE OF CORRECTION

PATENT NO. : 8,603,028 B2
APPLICATION NO. : 13/422919
DATED : December 10, 2013
INVENTOR(S) : Christopher S. Mudd et al.

It is certified that error appears in the above-identified patent and that said Letters Patent is hereby corrected as shown below:

In the Specification

In column 2, line 39, delete “AND” and insert -- and --, therefor.

In column 8, lines 34-35, delete “Prilocalne,” and insert -- Prilocaine, --, therefor.

In column 10, line 26, delete “later” and insert -- latter --, therefor.

Signed and Sealed this
Twenty-sixth Day of May, 2015

Michelle K. Lee
*Director of the United States Patent and Trademark Office*